United States Patent [19]
Adamski et al.

[11] Patent Number: 5,185,126
[45] Date of Patent: Feb. 9, 1993

[54] INFECTIOUS WASTE DISPOSAL UNIT

[75] Inventors: Joseph R. Adamski, Sudbury; Robert F. Bowen, Burlington; Robin C. Hossfield, Medway; Thomas P. Schregardus, Somerville; John S. Sklenak, Sudbury, all of Mass.

[73] Assignee: Raytheon Company, Lexington, Mass.

[21] Appl. No.: 727,719

[22] Filed: Jul. 10, 1991

[51] Int. Cl.[5] .............. A61L 2/00; G05D 23/00; F27B 14/06; G01F 23/00
[52] U.S. Cl. .......................... 422/38; 422/24; 422/106; 422/307; 422/109; 75/290 V; 219/421; 219/424; 432/156
[58] Field of Search ............ 422/1, 24, 105, 106, 422/109, 307, 38; 432/157, 158, 160, 156; 219/400, 421, 424; 110/250; 126/21 A; 220/908; 73/290 V; 340/621

[56] References Cited

U.S. PATENT DOCUMENTS

| | | | |
|---|---|---|---|
| 3,465,124 | 9/1969 | Sauer | 126/21 A |
| 3,831,514 | 8/1974 | Jernstrom | 422/24 |
| 4,071,738 | 1/1978 | Jenn et al. | 219/400 |
| 4,114,441 | 9/1978 | Magri | 73/290 V |
| 4,155,294 | 5/1979 | Langhammer et al. | 99/427 |
| 4,332,992 | 6/1982 | Larsen et al. | 219/10.55 R |
| 4,865,814 | 9/1989 | Childress | 422/116 |
| 4,902,482 | 2/1990 | Faust | 422/121 |
| 4,935,604 | 6/1990 | Allen et al. | 219/400 |
| 4,971,764 | 11/1990 | Albright | 422/110 |

FOREIGN PATENT DOCUMENTS

9014847 12/1990 World Int. Prop. O. ............ 422/1

Primary Examiner—Robert J. Warden
Assistant Examiner—T. A. Trembley
Attorney, Agent, or Firm—Judith A. Caplan; Richard M. Sharkansky

[57] ABSTRACT

A system for safely disposing of pathogenic waste materials. The waste material is disposed in a chamber and heated by forced hot air to temperatures above approximately 450° F. to destroy harmful bacteria within several minutes. The high temperatures melt plastic waste materials. The harmless waste is cooled providing a solid block in which syringes and other sharp items are generally encased. The temperature within the chamber is continuously sensed and the operation of the apparatus is microprocessor controlled to adjust the process time in accordance with the load size. The microprocessor further stores the sensed temperature to provide verification that the waste has been exposed to sufficient temperatures and for a sufficient time to render such waste harmless.

18 Claims, 6 Drawing Sheets

INFECTIOUS WASTE DISPOSAL UNIT

BACKGROUND OF THE INVENTION

This invention relates generally to waste disposal and more particularly to an improved system for sterilizing infectious waste.

As is known in the art, waste disposal is an issue of growing public concern. Increasing quantities of waste are causing landfills to reach maximum capacity sooner than anticipated. As a result, municipalities are being forced to transport waste to remote processing facilities at considerable cost.

As is also known in the art, the disposal of infectious, or pathogenic waste presents a variety of concerns. In particular, the AIDS epidemic has heightened awareness of the risks involved with handling pathogenic waste materials. Additionally, recent incidents of medical waste appearing along coastal waterways has prompted government regulations regarding the disposal of medical refuse.

Various techniques are currently utilized for the disposal of infectious waste material. The most common method for processing infectious waste is incineration. A hospital may have an incinerator located at the facility or, alternatively, may transport its waste to an incinerator at an off-site location. Shipping the waste to an off-site incinerator is, generally, less expensive since the cost of the incinerator, as well as its maintenance is avoided. On the other hand, having an incinerator located at the hospital may reduce the risk of infection to the individuals who transport the refuse due to the fact that the waste is carried a shorter distance. However, while the risk of infection to the waste handler is reduced as the distance that the waste is transported is reduced, the risk still exists when any transport of infectious material is required. For example, the individual carrying a bag of contaminated material may inadvertently hit the bag against a wall or drop the container causing it to tear and waste to leak out. Also, sharp objects, such as hypodermic syringes or broken glass from items used for cultures or tissue specimens, may puncture the bag as well as the individual transporting it.

An equally serious concern regarding the use of incinerators is that certain materials yield ash which may contain carcinogenic or other hazardous materials. Relatively costly precautions are generally required to ensure that the emissions are non-toxic. Furthermore, the certification required to operate an incinerator may be difficult to obtain.

More recently, microwave energy has been investigated as an alternative means for sterilizing contaminated waste. Microwave energy may be used to heat the medical waste to a suitable disinfecting temperature or, alternatively, to a temperature which will incinerate the waste. However, the cost of microwave energy generally exceeds that of conventional energy sources and, thus, microwave energy may be an unnecessarily expensive alternative.

Alternatively, infectious waste may be processed in an autoclave in which sterilization results from exposure to steam. Generally, this technique is utilized with re-usable instruments and containers. While autoclaving may be suitable to render infectious materials sterile for re-use, non-sterilized items can be easily mistaken for ones which have been processed in the autoclave. Thus, a serious risk of exposure to infected re-usable materials exists.

Autoclaving may also be used to disinfect disposable items prior to depositing such items in a landfill. However, as a result of the growing public concern regarding pathogenic waste, an emerging requirement has been that the waste not only be rendered harmless but also unrecognizable as medical refuse prior to being deposited in a landfill. Since, during autoclaving the medical containers and instruments are left intact after being disinfected, autoclaving does not render the medical waste unrecognizable as such.

As is also known in the art, another method of infectious waste disposal includes autoclaving in conjunction with exposure to air heated to temperatures high enough to melt the plastic waste. This method is suitable since today, medical instruments and containers are predominantly made of plastic. An example of this type of waste disposal unit is described in U.S. Pat. No. 3,958,936. In this unit, air is heated to a temperature of at least 450° F. and is directed to a melting chamber in which the infectious waste is disposed. The heated air melts the plastic waste material to a flowable state. An afterburner exhaust arrangement is used to incinerate the vapors evolved during the melting process. When the heating and melting cycle is completed, the chamber is allowed to cool. Upon cooling, the melted material solidifies into a block which can be easily removed and disposed of. Thus, this arrangement renders the pathogenic material harmless and unrecognizable as medical waste. Also, generally, items such as needles and surgical blades will become embedded in the resulting solid block thereby reducing the likelihood of such needles injuring the waste handler. Additionally, the volume of the waste is reduced by the melting process.

SUMMARY OF THE INVENTION

It is an object of the present invention to provide a an improved system for sterilizing infectious waste.

A further object of the present invention is to provide a safe method for disposing of infectious waste at the location where the waste is generated.

Another object of the invention is to provide apparatus for reducing the volume of the infectious waste and for rendering the disinfected material unrecognizable as medical waste.

A yet further object is to monitor the sterilization process to provide a record of the sterilization.

A further object of the invention is to provide a waste disposal system operable either on a continuous basis or in a batch mode.

A still further object of the present invention is to provide an infectious waste sterilization system having a simple and effective exhaust arrangement.

Yet another object is to provide a sterilization system having semi-forced cooling.

These and other objects of the present invention are provided by sterilization apparatus including a cabinet having a melting chamber disposed therein. The melting chamber has an aperture through which waste material is deposited and a cover disposed over the aperture. An air circulation system includes a first air circulation chamber disposed on a first side of the melting chamber and communicating therewith, a second air circulation chamber disposed on a second side of the melting chamber and communicating therewith, and a heating element disposed in the first air circulation chamber. The air circulation system further includes a first blower for directing air into the first air circulation chamber, past the heating element, through the melting chamber, and into the second air circulation chamber. An exhaust duct is coupled to the first air circulation chamber and directs air out of such chamber. A second blower is coupled to the exhaust duct and directs air through the exhaust duct to mix with the air directed out of the first air circulation chamber.

With such an arrangement, apparatus for sterilizing infectious waste material is provided with a simple, inexpensive, and effective exhaust arrangement, as contrasted to the afterburner arrangement described in the above-reference U.S. Pat. No. 3,958,936. More particularly, plastic waste material is melted in the melting chamber and the vapors evolving from the melting process are directed therefrom through the exhaust duct. In the exhaust duct, vapors from the melting chamber mix with air directed by the second blower before being directed out of the sterilization apparatus.

In accordance with a further feature of the present invention, the cabinet has an inlet and the air circulation system further includes an inlet duct coupled to the second air circulation chamber for directing air from the cabinet inlet into the second air circulation chamber. A valve is coupled to the inlet duct for opening and closing the duct, and a controller is provided for de-activating the heating element and activating the blower when the inlet duct is open.

This arrangement provides semi-forced cooling to the sterilization apparatus and to the melted waste material disposed therein once the sterilization process is completed. More particularly, when the sterilization, or melting process is completed, the valve is opened, the heating element is shut off, and the blower remains activated. Thus, air is directed from outside of the cabinet, through the cabinet inlet, through the inlet duct, and into the second air circulation chamber. From the second air circulation chamber, the air is directed by the blower into the first air circulation chamber and through the melting chamber. Since the heating element is shut off when the valve is opened, the air entering the melting chamber through the inlet duct is circulated without being heated. In other words, the same blower that circulates the heated air during the melting process, circulates the cooler air entering the cabinet through the inlet after such process is completed and during a cooling period. In this way, the added cost and space requirements associated with additional cooling apparatus is eliminated. Furthermore, the semi-forced cooling thus provided decreases the total sterilization time, as contrasted to the apparatus of the above-referenced U.S. Pat. No. 3,958,936, thereby increasing the waste throughput.

In accordance with another feature of the invention, apparatus for sterilizing waste material includes a cabinet, a melting chamber disposed within the cabinet and having an aperture through which waste material is deposited, and an air circulation system comprising a heating element and a blower. The apparatus further includes a drawer for loading waste material into the melting chamber through the aperture. The drawer is movable between a first loading position and a second position in which the drawer is disposed substantially above the aperture. Preferably, the apparatus further includes a cover disposed over the aperture and having the drawer coupled thereto.

With such a cover arrangement, the sterilization apparatus may be operated in either a continuous mode or a batch mode. Specifically, waste material may be deposited in the drawer on a continuous basis. The drawer may then be moved over the aperture of the melting chamber causing the waste material to drop into the chamber. Continuous mode operation may be desirable when the apparatus is disposed in operating environments in which infectious waste material is continuously generated. Alternatively, waste material may be accumulated and then deposited directly into the melting chamber through the aperture therein by opening the cover. Such batch mode operation may be desirable in applications where the sterilizer is disposed at a distance from the location where the waste is generated.

In accordance with a further feature of the invention, the apparatus includes a temperature sensor disposed within the cabinet for continuously sensing temperature and means coupled to the temperature sensor for providing a record of a plurality of sensed temperatures. With this arrangement, the temperature within the cabinet, and more particularly, that of the waste material disposed therein, is measured to provide a record of sensed temperatures. In this way, assurance is provided that the waste material was in fact exposed to suitable bacteria sterilizing temperatures for a suitable duration and thus, that the apparatus is functioning properly.

Another feature of the present invention provides a method for sterilizing waste material in a cabinet comprising the steps of providing a melting chamber in the cabinet, providing a first air circulation chamber on a first side of the melting chamber in communication therewith, and providing a second air circulation chamber on a second side of the melting chamber also in communication therewith. A heating element is provided in the first air circulation chamber. The air is directed into the first air circulation chamber, past the heating element, and into the second air circulation chamber. Additional steps include sensing temperature within the cabinet and recording a plurality of sensed temperatures.

As with the preceding feature, the above-described sterilization method provides a record of sensed temperatures. Such a record is desirable for verifying the sterilization process.

In accordance with a still further feature of the present invention, sterilization apparatus includes a cabinet and a melting chamber disposed within the cabinet. The chamber has an aperture through which waste material is deposited to a predetermined height. An air circulation system includes a heating element and a blower, with the blower directing air past the heating element and into the melting chamber. A cover is disposed over the aperture and a sonic device is disposed over the melting chamber and in alignment with the aperture. The sonic device provides a control signal corresponding to the height of the waste material disposed in the chamber. The apparatus further includes means responsive to the control signal for de-activating the heating element.

With this arrangement, the melting cycle duration may be extended beyond the time required to sterilize the waste in order to provide maximum, or a desired volume reduction of the waste. In other words, once the sterilization process is completed, the heating element remains activated and the height of the waste is monitored to determine when no further volume reduction is occurring or, alternatively, when a predetermined desired volume reduction has been achieved. The heating element is de-activated in response to such determination.

The above described apparatus may further include a drawer coupled to the cover for loading waste material into the melting chamber through the aperture and a lock mechanism. The drawer is moveable between a first loading position and a second position in which the drawer is disposed substantially above the aperture. The lock mechanism locks the drawer in the first loading position in response to the control signal provided by the sonic means. More particularly, the drawer is locked in the first loading position when the control signal indicates that the height of the waste disposed in the melting chamber has reached a predetermined level. This arrangement prevents an operator of the sterilizer from attempting to load waste material into the melting chamber once such chamber is filled to capacity.

The apparatus may additionally include a lid disposed over the drawer when the drawer is disposed in the first loading position and a lock mechanism responsive to the control signal provided by the sonic means for locking the lid in a closed position. As above, this feature prevents an operator of the sterilizer from attempting to load waste material into the melting chamber via the drawer once such chamber is filled to capacity.

An additional feature of the invention provides a method for sterilizing waste material in a cabinet and includes the steps of providing a melting chamber in the cabinet in which the waste material is deposited, providing a first air circulation chamber on a first side of the melting chamber and in communication therewith, and providing a second air circulation chamber on a second side of the melting chamber and in communication therewith. A heating element is provided in the first air circulation chamber. Additional steps include sensing the height of the waste material deposited in the chamber. The method may further comprise the step of de-activating the heating element in response to the sensed height.

With the above-described method of sterilizing waste material, maximum, or a desirable amount of volume reduction of the waste is achieved. Such is achieved by sensing the height of the waste material and de-activating the heating element in response to such height. In this way, the process time may be extended beyond the necessary bacteria sterilization time to provide a further reduction in the volume of the waste.

BRIEF DESCRIPTION OF THE DRAWINGS

The foregoing features of this invention, as well as the invention itself may be more fully understood from the detailed description of the drawings, in which.

DESCRIPTION OF THE PREFERRED EMBODIMENTS

Figure 1:
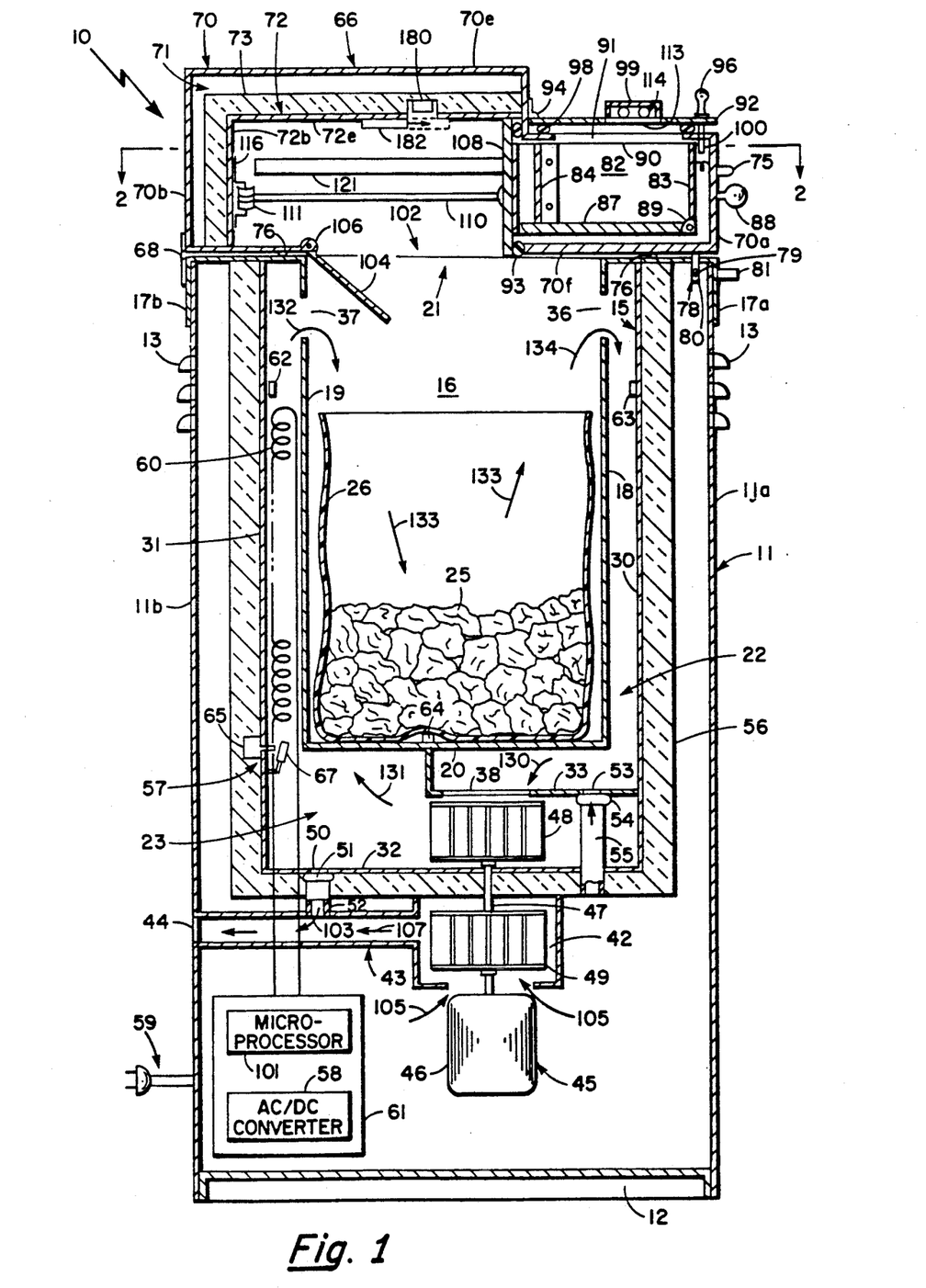
FIG. 1 is a side elevational view partly in section of a waste disposal system in accordance with the present invention.

Referring now to FIG. 1, an infectious waste sterilizer 10 includes a base 12 and an outer cabinet 11. Here, cabinet 11 is made of stainless steel; however, alternatively such cabinet 11 may be made of any material having suitable rigidity and strength. Cabinet 11 has a front wall 11a, a rear wall 11b, and sidewalls (not labelled) attached together by any suitable means such as welding. Cabinet 11 includes inlets 13 disposed through front wall 11a and rear wall 11b of outer cabinet 11, as shown, which provide a path for air from outside cabinet 11 to enter cabinet 11, as will be described hereinafter.

An inner housing 15 is disposed inside cabinet 11 and is shaped to provide a melting chamber 16. More particularly, housing 15 is defined by a front wall 30, a rear wall 31, a bottom wall 32, and side walls (not labelled). Here, housing 15 further includes flanges 17a and 17b which are bent over a top portion of front wall 11a and rear wall 11b, respectively, and are suitably attached thereto. Melting chamber 16 is disposed within inner housing 15 and further includes a front chamber wall 18, a rear chamber wall 19, a bottom chamber wall, or floor 20, and chamber side walls (not shown). Melting chamber 16 has an aperture 21 disposed in a top portion thereof through which waste material 25 is deposited. Here, such waste material 25 is disposed in a bag, or pouch 26 within melting chamber 16. The use of bag 26 facilitates the handling of the waste material 25 prior to its disposal in sterilizer 10 and may also aid in the removal of the safe, sterilized waste, as will be further described below. The bag 26 is, here, made of a plastic material which is capable of withstanding temperatures in excess of approximately 450° F. An example of a suitable material for bag 26 is IPPLON WN1500 manufactured by International Plastic Products, Inc., of Carson, Calif. However, bags or containers made of metal such as aluminum foil may be used. Furthermore, it may be desirable to provide handles, either integrally formed with and extending vertically from such a pan or adapted for attaching to such pan, in order to further facilitate removal of the sterilized waste. Alternatively, re-usable pans made of a suitable material having a release coating such as Teflon may be used. Alternatively, infectious waste material 25 may be deposited directly into melting chamber 16 without the use of a bag 26. Note however that it may be desirable to coat the interior of melting chamber 16 with a material such as Teflon, in order to prevent waste material 25 deposited directly therein (i.e. without a bag 26) from sticking to melting chamber 16. Here, melting chamber 16 has a capacity of approximately one thousand cubic inches.

Melting chamber 16 has an insulating material with suitable thermal insulation properties disposed therein. Here, front chamber wall 18, rear chamber wall 19, and chamber side walls (not shown) have an approximately one inch thick layer of "Lo-Con Felt Carborundum Fiberfrax" disposed thereover, such material being manufactured by Standard Oil's Fibers Division of Niagara Falls, N.Y. This material assists in retaining heat within melting chamber 16, as well as keeping the cabinet 11 at a safe temperature for contact by operating personnel. Insulation 56 is disposed around the exterior of housing 15, as shown, to further aid in retaining heat within chamber 16.

Disposed externally to melting chamber 16 and within inner housing 15 are a front air circulation chamber 22 and a rear air circulation chamber 23. Chambers 22 and 23 are separated by a divider 33 disposed between, and attached to, front wall 30 of inner housing 15 and bottom chamber wall 20, as shown. Thus, while the cross-section of FIG. 1 shows chambers 22 and 23 adjacent to front wall 11a and rear wall 11b of cabinet 11, respectively, it should be appreciated that such chambers 22 and 23 extend somewhat along the side walls of cabinet 11. Front chamber wall 18 has an aperture 36 disposed therethrough so that front air circulation chamber 22 communicates with melting chamber 16. Similarly, rear chamber wall 19 has an aperture 37 disposed therethrough so that rear air circulation chamber 23 also communicates with melting chamber 16.

A blower 45 disposed below melting chamber 16 includes a motor 46, a drive shaft 47, and two impellers 48 and 49. Impeller 48 is disposed in the rear air circulation chamber 23. An aperture 38 is disposed through divider 33. In this way, front air circulation chamber 22 communicates with rear air circulation chamber 23, or more particularly, with impeller 48. A blower chamber 42 is, here, disposed below rear air circulation chamber 23 and has impeller 49 disposed therein.

An outlet arrangement 43 is coupled between rear air circulation chamber 23 and blower chamber 42 and directs air out of cabinet 11. More particularly, an exhaust duct 52 extends between outlet arrangement 43 and an aperture 50 disposed through bottom wall 32 of housing 15. In this way, the exhaust arrangement 43 communicates with rear air circulation chamber 23. A valve 51 is coupled to exhaust duct 52 and regulates the air flow through aperture 50, as will be described hereinafter. Suffice it here to say that air is directed out of rear air circulation chamber 23, through duct 52 and, further, through outlet arrangement 43. An outlet aperture 44, here disposed through rear wall 11b of cabinet 11, is coupled to outlet arrangement 43 and is further adapted for coupling to a suitable fume hood arrangement, or a venting duct (not shown). Thus, the air directed through outlet arrangement 43 exits cabinet 11 through outlet aperture 44.

An inlet duct 55 extends from divider 33 to the bottom wall 32 of housing 15 and directs air from outside of cabinet 11 through inlets 13 and into front air circulation chamber 22. More particularly, an aperture 53 is disposed through divider 33 and is coupled to inlet duct 55. A valve 54 is coupled to inlet duct 55 to control the flow of air therethrough as will be described.

An electrical heating element 60 is disposed inside rear air circulation chamber 23 and is controlled by conventional means disposed within a control compartment 61. Here, heating element 60 is a "Calrod" device manufactured by Chromalox of Pittsburgh, Pa. A power cord and plug arrangement 59 is adapted for coupling to a standard 120 volt alternating current source which provides power for, inter alia, heating element 60. Additionally, a conventional alternating current (AC) to direct current (DC) converter 58 (shown schematically) is disposed in control compartment 61 and provides a DC power source for electronics such as a microprocessor 101 also disposed in the control compartment 61. The function of microprocessor 101 will be described hereinafter.

An air flow indicator 57 is disposed in rear air circulation chamber 23 and includes a switch 65 and a paddle 67. Paddle 67 is rigidly attached to rear wall 31 of housing 15 by any suitable means, but is flexible in that paddle 67 sways toward switch 65 in response to a flow of air thereby in the direction indicated by arrow 131. Thus, when blower 45 is activated, thereby activating impeller 48 (as well as impeller 49), the airflow, as shown by arrow 131, forces paddle 67 to sway and contact switch 65. When paddle 67 contacts switch 65, switch 65 is activated. Switch 65 is coupled to microprocessor 101 and, when activated, provides an indication that air is flowing inside sterilizer 10 (i.e. that blower 45 is operating properly).

Temperature sensing devices 62-64 are used to measure the temperature at various locations within the sterilization apparatus 10. More particularly, disposed in rear air circulation chamber 23 and adjacent to heating element 60 is temperature sensing device 62. Temperature sensing device 62 provides continuous temperature sensing in order to modulate the "on" and "off" time of heating element 60. Temperature sensing device 63 is, here, a switch and is disposed in front air circulation chamber 22 to provide an indication of whether the air inside sterilizer 10 is at a temperature which is safe for contact by the operator of sterilizer 10. In other words, temperature switch 63 operates as an over temperature indicator. When the temperature inside sterilizer 10 is greater than approximately 525° F., switch 63 is activated and causes the heating element 60 to be shut off and an audio indicator to be activated, as will be described in conjunction with FIGS. 5A and 5B. A third temperature sensing device 64 is, here, disposed inside melting chamber 16 near the center of the floor 20 thereof, as shown. Temperature sensor 64 provides an indication of the temperature of the waste material 25 due to its placement proximate to, and here under, such waste 25. Here, temperature sensing devices 62 and 64 are conventional thermocouple devices and sensing device 63 is a thermally activated switch; however, alternatively, it is noted that either fewer or more temperature sensing devices may be utilized, and such devices may be of any suitable type. Although not shown, temperature sensing devices 62-64 are coupled to microprocessor 101.

The indication of the temperature of waste material 25 here, provided by temperature sensor 64, may be stored and accessed by the operator of sterilizer 10. For example, microprocessor 101 has the capability of storing a plurality of sensed temperature values. Alternatively, additional memory capability may be provided with a conventional memory device. The temperature values thus stored may be accessed by the operator of sterilizer 10 in various ways. A printer (not shown) may be provided on the sterilizer 10, such printer communicating with microprocessor 101 to provide a printout of successive temperature measurements automatically and continuously during the sterilization process. Alternatively, such a printout may be provided only on demand by the operator. The printer may be part of sterilizer 10 or may be provided as a separate device adapted for coupling to an appropriate connector or jack (not shown) on sterilizer 10, thereby communicating with microprocessor 101. Another alternative is to provide a connector or jack compatible with a computer, such as an RS232 connector, so that the temperature information may be accessed by such computer. In each of the above-described arrangements, the operator of sterilizer 10 is provided with a record of a plurality of sensed temperatures within the cabinet. Stated differently, the temperature within the cabinet (corresponding to the temperature of waste 25) is continuously sensed during the sterilization process and a record of such sensed temperatures provided. In this way, the operation of sterilizer 10 and the fact that the waste 25 has been sterilized may be verified.

Figure 2:
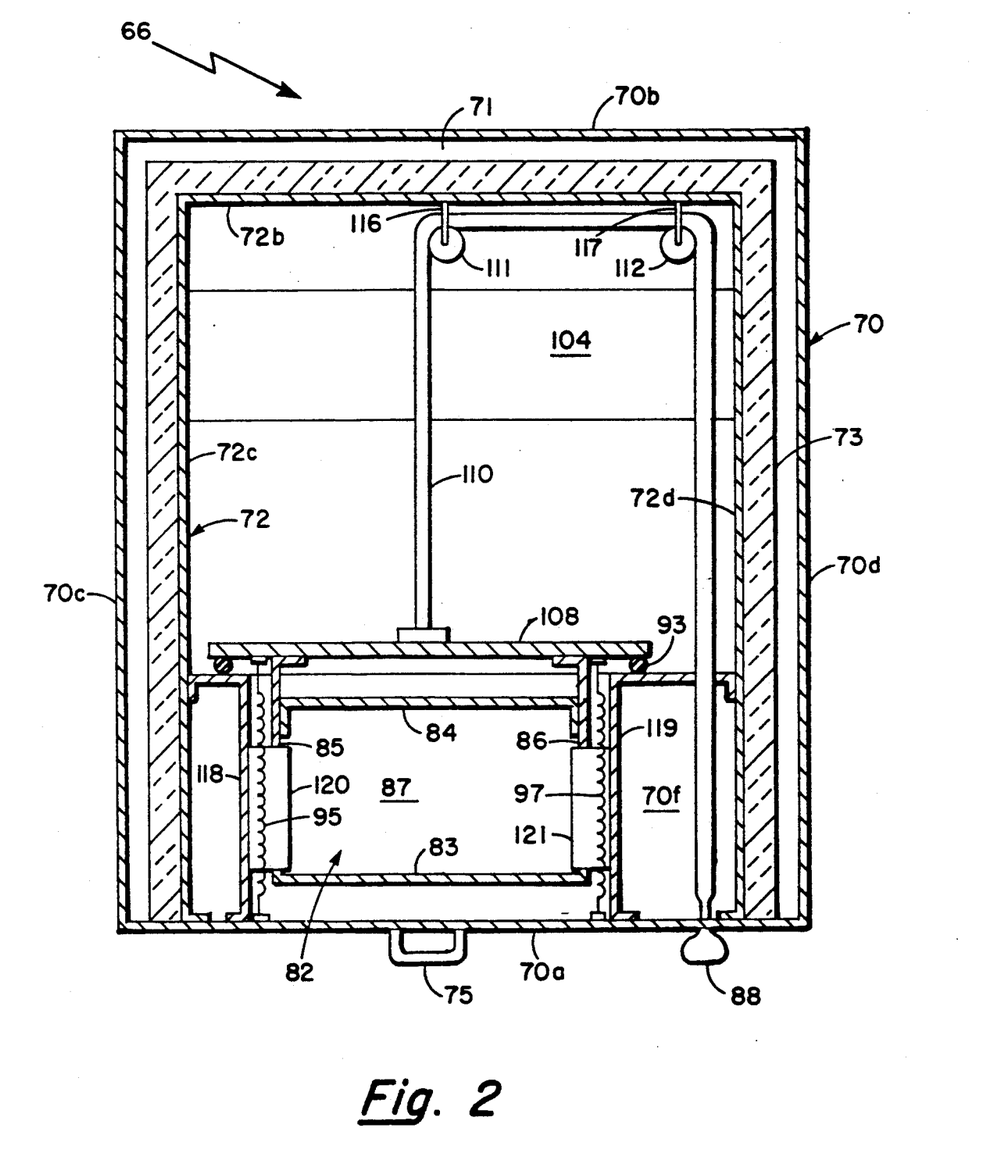
FIG. 2 is a cross-sectional view of the waste disposal system taken along lines 2—2 of FIG. 1.

Referring now to FIGS. 1 and 2, a cover 66 is disposed over the aperture 21 of melting chamber 16. Here, cover 66 is made of stainless steel and is attached to rear wall 11b of cabinet 11 by a hinge 68. However, it is noted that cover 66 may alternatively be made of other materials having suitable strength and rigidity. Cover 66 includes an outer frame 70 defined by a front wall 70a, a rear wall 70b, side walls 70c and 70d (FIG. 2), a top wall 70e and a partial bottom wall 70f. An inner frame 72 of cover 66 is attached to outer frame 70 by any suitable means such as welding and has insulation 73 attached externally thereto, as shown. Inner frame 72 is defined by a rear wall 72b, side walls 72c and 72d (FIG. 2), and a top wall 72e (FIG. 1). Disposed between insulation 73 and outer frame 70 is a vacant area, or air gap 71. Air enters air gap 71 through openings (not shown) in outer cover frame 70 and flows therethrough by natural convection. Such air flow cools the cover 66 which may become warm during the sterilization process.

Disposed on the front wall 70a of outer frame 70 is a handle 75 with which cover 66 may be lifted to an open position to expose melting chamber 16. Alternatively, cover 66 may be lowered over cabinet 11 to a closed position, as shown, to conceal melting chamber 16. A seal 76, here made of silicone rubber, is disposed around the entire perimeter of aperture 21 (i.e. on flanges 17a and 17b) so that, when cover 66 is lowered over cabinet 11, seal 76 is compressed and effectively isolates the atmosphere inside melting chamber 16 from the atmosphere external to such chamber 16. It is desirable to seal melting chamber 16 so that fumes, evolving from the melting process, do not escape into the atmosphere external to the sterilizer 10.

An interlock mechanism 78 (FIG. 1) allows cover 66 to be locked when such cover 66 is lowered over cabinet 11. Locking the cover 66 in a lowered, or closed position is desirable to ensure that operators of the sterilizer 10 do not raise the cover 66 during the sterilization process or shortly thereafter, when the contents of melting chamber 16 and the chamber 16 itself may be dangerously hot. Here, an extending rod 80 is attached, by any suitable means such as welding, to the bottom wall 70f of outer cover frame 70. Rod 80 has an aperture, or eyelet (not labelled), disposed therethrough. When cover 66 is lowered over cabinet 11, rod 80 is aligned with an aperture (not labelled) in cabinet 11, or more particularly, in flange 17a. Thus, when cover 66 is in its lowered position, as shown in FIG. 1, rod 80 extends down into cabinet 11. In this position, a pin 79 can be moved horizontally into the eyelet of rod 80 thereby locking the cover 66 in a closed position. Here, an interlock lever 81, disposed on front wall 11a, is turned to move the pin 79 through the eyelet to lock cover 66. A solenoid which, upon activation, moves the pin 79 through the eyelet of rod 80, as well as other suitable interlock mechanisms, may alternatively be used.

Figure 3:
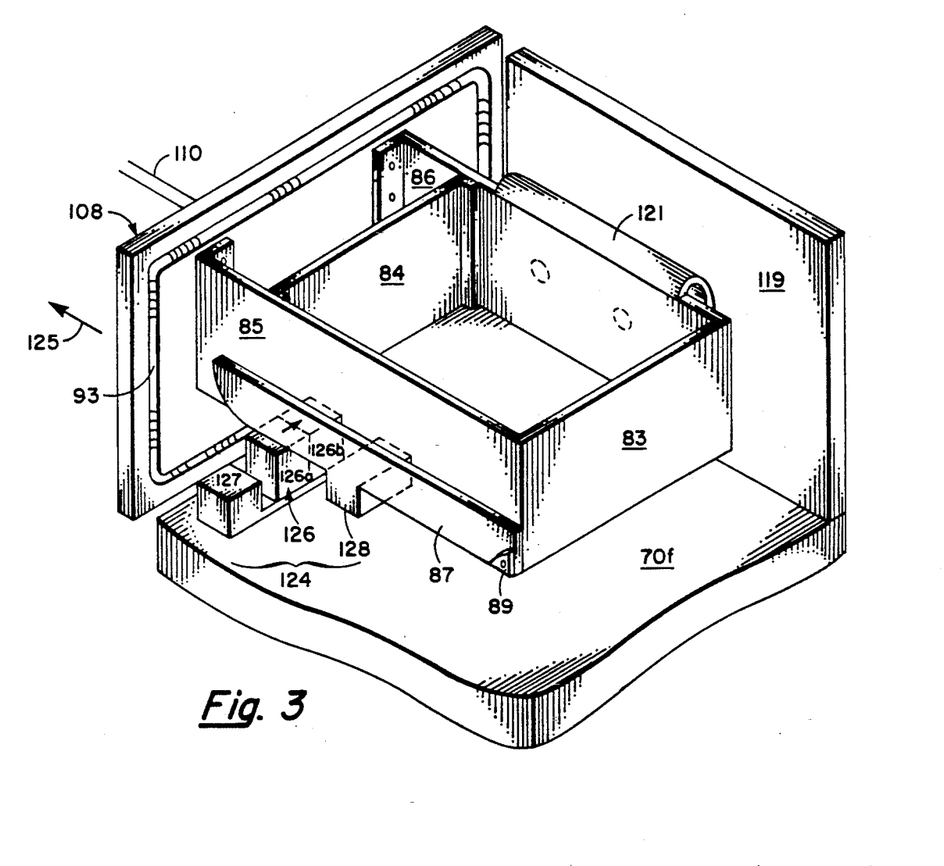
FIG. 3 is a somewhat simplified isometric view of a portion of the waste disposal system of FIG. 1.

Disposed within cover 66 is a drawer 82 into which medical waste 25 may be deposited and subsequently transferred to melting chamber 16, as described below. Drawer 82 is defined by a front wall 83, a rear wall 84, side walls 85 and 86 (FIG. 2), and a bottom wall, or floor 87 and has a capacity of approximately one hundred cubic inches. Front wall 83 and bottom wall 87 are attached together by a hinge 89, as shown in FIGS. 1 and 3. Drawer 82 has an aperture 90 disposed in a top portion thereof. Disposed over aperture 90 and aligned therewith, is an aperture 91 disposed through the top wall 70e of outer cover frame 70. A lid 92 is disposed over aperture 91 and is attached to the top wall 70e by a hinge 94. Lid 92 has a knob 96 disposed thereon with which lid 92 may be raised. When lid 92 is in a raised, or open position, drawer 82 is exposed and accessible. A seal 98, here made of silicone rubber, is disposed between cover 66 and lid 92 when lid 92 is in the closed position, as shown. More particularly, here, seal 98 is attached to the bottom surface of lid 92 such that when lid 92 is lowered over aperture 91 in a closed position, seal 98 is compressed and effectively isolates the interior atmosphere of melting chamber 16 from the exterior thereof. An interlock mechanism 100 is provided to allow lid 92 to be locked in the closed position. Such interlock mechanism 100 may be of the type described above in conjunction with cover interlock mechanism 78, or any other suitable device for ensuring that lid 92 will not be opened when the temperature inside sterilizer 10 is so hot as to be dangerous to operating personnel.

A portion of lid 92 may be comprised of an ultraviolet transmissive material, or window 113 and an ultraviolet lamp 114 with a suitable cover 99 disposed thereover may be disposed external to drawer 82, as shown. When ultraviolet lamp 114 is activated, window 113 permits transmission of ultraviolet radiation therefrom to be directed into drawer 82. An example of a material for window 113 having suitable ultraviolet transmissivity is sold under the trade name of Lexan by General Electric of Pittsfield, Mass. When activated, ultraviolet lamp 114 directs ultraviolet radiation into drawer 82 to sterilize any bacteria contained therein. This feature may be desirable in cases where there is concern that infectious waste remaining in drawer 82 during the sterilization process may not be rendered harmless, as will be described.

Cover 66 has an aperture 102 disposed in the bottom wall 70f thereof and aligned with aperture 21 of melting chamber 16 when such cover 66 is in the lowered position, as shown in FIG. 1. A deflector 104, here made of stainless steel, is attached to the bottom wall 70f of cover 66 by a hinge 106. Deflector 104 extends down into melting chamber 16 to direct waste material 25 from drawer 82 into melting chamber 16, as will be described hereinafter. It is noted that deflector 104 may, alternatively, be integrally formed with the bottom wall 70f of cover 66 rather than being hingedly coupled thereto, as shown.

Referring now to FIGS. 1 to 3, a flange 108 is disposed adjacent rear wall 84 of drawer 82. More particularly, here, the side walls 85 and 86 of drawer 82 are attached to flange 108 by any suitable means such as by bolting or welding. A cable 110 is coupled to flange 108 by any suitable means and extends back toward rear wall 72b of inner cover frame 72. More particularly, cable 110 engages with two pulleys 111 and 112 which guide the cable 110 from flange 108 to a knob 88 disposed externally to front wall 70a, as shown in FIG. 2. Pulleys 111 and 112 are mounted to rear wall 72b of inner cover frame 72 by pulley supports 116 and 117, respectively.

A pair of support walls 118, 119 are attached to side walls 72c and 72d of inner cover frame 72, respectively (FIG. 2). A corresponding pair of brackets 120 and 121 are attached to the support walls 118 and 119, respectively. Springs 95 and 97 are disposed, here, above brackets 120 and 121, respectively, and are attached between flange 108 and front wall 70a by any suitable means.

In operation, drawer 82 slides along brackets 120 and 121 toward the rear wall 72b in response to knob 88 being pulled outward, or away from cabinet 11, as will be described below. Drawer 82 is moveable between a first loading position (i.e. the forward position) in which waste material may be deposited therein and a second position in which the drawer is disposed substantially above aperture 21 of melting chamber 16 to transfer waste 25 from drawer 82 into melting chamber 16, as will be described. More particularly, conventional brackets 120 and 121 extend backwards to support drawer 82 as such drawer 82 slides backwards. Springs 95 and 97, bias drawer 82 to the forward position, as shown in FIG. 1. When drawer 82 is in the forward position, a seal 93 is disposed between flange 108 and adjacent portions of cover 66, as shown. More particularly, here, seal 93 is made of silicone rubber and is attached to flange 108 such that when drawer 82 is in the forward position, seal 93 is compressed. In its compressed position, seal 93 effectively isolates drawer 82 from melting chamber 16.

Referring now specifically to FIG. 3, an interlock mechanism 124 is disposed below drawer 82 and permits such drawer 82 to be locked in the forward position. Interlock mechanism 124 is desirable for several reasons. First, by locking drawer 82 in its forward position during the melting cycle, an operator of sterilizer 10 is prevented from pulling handle 88 to slide drawer 82 over melting chamber 16, thereby transferring waste from drawer 82 to melting chamber 16, during such melting cycle. In other words, the possibility of infectious waste 25 being introduced from drawer 82 into the melting chamber 16 at a stage of the melting cycle when it will not be sufficiently heated in order to render it harmless is avoided. Secondly, the drawer interlock mechanism 124 provides an additional level of protection in the event that the lid interlock mechanism 100, which generally would lock the lid 92 closed during the melting cycle, were to fail. In other words, even if an operator had access to the drawer 82 during the melting cycle, the interlock mechanism 124 would prevent the drawer 82 from being moved backward over the melting chamber 16 during such cycle. In this way, the seal 93 is maintained in a compressed position during the melting cycle to prevent the dangerously hot air inside chamber 16 from escaping.

Here, drawer interlock mechanism 124 is comprised of a sliding latch portion 126 and a projecting portion 128. More particularly, the bottom wall 87 of drawer 82 has a projecting porting 128 extending downward therefrom. The sliding latch portion 126 is disposed on the bottom wall 70f of outer cover frame 70 and, in an unlocked position 126a, allows drawer 82 to slide backwards (as shown by arrow 125) along brackets 120 and 121 without interference. A solenoid 127 is disposed adjacent to sliding latch portion 126 and, upon activation, moves such portion 126 to a locked position 126b. In the locked position 126b, drawer 82 is prevented from sliding backwards (as shown by arrow 125) since sliding latch portion 126 interferes with such motion. In other words, when sliding latch portion 126 is in the locked position 126b, projecting portion 128 contacts latch portion 126 if the operator of the sterilizer 10 tries to move drawer 82 backwards by pulling knob 88. In this way, the backward sliding of drawer 82 is prevented when sliding latch portion 126 is in locked position 126b.

In operation, infectious waste material 25 may be deposited into drawer 82 by opening lid 92, or, alternatively, may be deposited directly into melting chamber 16 by raising cover 66. For example, in applications where relatively small amounts of infectious waste 25 are generated on a continuous basis, it may be desirable to utilize the drawer 82 to dispose of such waste 25. Thus, the use of drawer 82 would tend to be convenient when sterilizer 10 is located, for example, in a physician's office or a medical laboratory environment at the location where relatively small amounts of waste are continuously generated. However, if sterilizer 10 is disposed some distance away from the source of the medical waste 25, for example in the basement of a hospital rather than in individual medical laboratories therein, it may be desirable to collect the medical waste 25 in a bag 26 and dispose of such bag 26 periodically rather than continuously. Also, if relatively large amounts of waste 25 are being generated, it may be preferable to deposit such waste 25 directly into melting chamber 16 rather than utilizing drawer 82.

Consider first the use of drawer 82 for the disposal of medical waste 25. The operator of sterilizer 10 opens lid 92 by pulling up on knob 96 to access drawer 82. With drawer 82 exposed, waste material 25 may be deposited directly therein. Once the waste 25 is deposited into drawer 82, the operator of sterilizer 10 closes lid 92. Thereafter, knob 88 is pulled outward from cabinet 11. Note that drawer interlock 124 may be activated to prevent the drawer 82 from sliding backwards until the lid 92 is closed and locked if so desired. As knob 88 is manually pulled outward, the cable 110 attached thereto is pulled accordingly. Thus, pulling knob 88 causes flange 108, to which cable 110 is attached, to slide backwards toward rear wall 72b. As flange 108 and, thus, drawer 82 slides backwards, bottom wall 87 of drawer 82 becomes aligned with the aperture 102 in cover 66. Since bottom wall 87 is not attached to rear wall 84, and is hingedly attached to front wall 83, when such bottom wall 87 moves over aperture 102, the end thereof distal from hinge 89 tilts downward. The downward tilting of bottom wall 87 causes the waste material 25 disposed thereon to drop out of drawer 82 and into melting chamber 16. Furthermore, deflector 104 is disposed such that when the medical waste 25 drops from downward tilted floor 87, deflector 104 directs such waste 25 downward toward the floor 20 of melting chamber 16. In this way, deflector 104 insures that the medical waste 25 will not enter aperture 37 in the rear chamber wall 19, thereby potentially contacting heating element 60. Although not shown, it may also be desirable to taper melting chamber 16 so that the walls thereof slope inward (i.e. so that floor 20 of chamber 16 is smaller in area than aperture 21 of chamber 16). Such tapering may assist in guiding the waste 25 to the floor 20 of chamber 16. Once the knob 88 has been pulled outward and the knob 88 is released, springs 95 and 97 contract to return drawer 82 to its forward position.

It is noted that, as an alternative to knob 88, the sliding of drawer 82 may be achieved by activating a button (not shown) disposed on front wall 11a of cabinet 11. In other words, when the drawer 82 is judged full by the operator, a "load" button may be activated. This action would automatically cause lid 92 to be locked in the closed position and drawer 82 to slide backwards over melting chamber 16, thereby transferring the waste 25 from the drawer 82 to the chamber 16.

It may be desirable to lock the lid 92 shut and/or the drawer 82 in the forward position when the melting chamber 16 has been filled with waste 25 to its maximum capacity. One way of determining when the melting chamber 16 has been filled with waste 25 is to use an ultrasonic sensor 180 (shown schematically in FIG. 1). More particularly, an ultrasonic transducer 180 may be disposed above melting chamber 16 and aligned with aperture 21. Ultrasonic transducer 180 is coupled to microprocessor 101 and provides a control signal corresponding to the duration between transmission of a sonic signal downward toward waste 25 and receipt of a reflection of such signal from waste 25. Such control signal is thus indicative of the height of such waste 25. The drawer interlock mechanism 124 and/or lid interlock mechanism 100 can be activated in response to the control signal to ensure that an operator of sterilizer 10 is prevented from attempting to deposit waste therein one chamber 16 is filled to capacity. A convenient location for such an ultrasonic sensor 180 is shown in FIG. 1. More particularly, the ultrasonic sensor 180 may be embedded in insulation 73 of cover 66, above melting chamber 16. Note that the excessive temperatures to which the inside of melting chamber 16 will be exposed during the melting cycle may require the ultrasonic sensor 180 to be shielded, for example by a sliding cover 182, to protect it from such temperatures. Such an arrangement may be realized by providing an aperture (not labelled) in the top wall 72e of inner cover frame 72, above which such sensor 180 is embedded in insulation 73, and also providing a sliding cover 182 (shown schematically in FIG. 1) thereover. With this arrangement, the sliding cover 182 may be automatically moved under the control of microprocessor 101 to expose the ultrasonic transducer 180 at appropriate times during the melting cycle, when the height of waste 25 is to be measured.

In accordance with an alternate mode of loading waste material 25 into chamber 16, cover 66 may be lifted by handle 75 to expose melting chamber 16. In this way, the operator of sterilizer 10 can deposit medical waste 25 directly into melting chamber 16 either with or without such waste 25 being contained in a bag 26. Medical waste 25 may thus be deposited in melting chamber 16 either via drawer 82, in what may be referred to as a continuous mode of operation, or by raising cover 66 and depositing the waste 25 directly into chamber 16, in what may be referred to as a batch mode operation.

Figure 4:
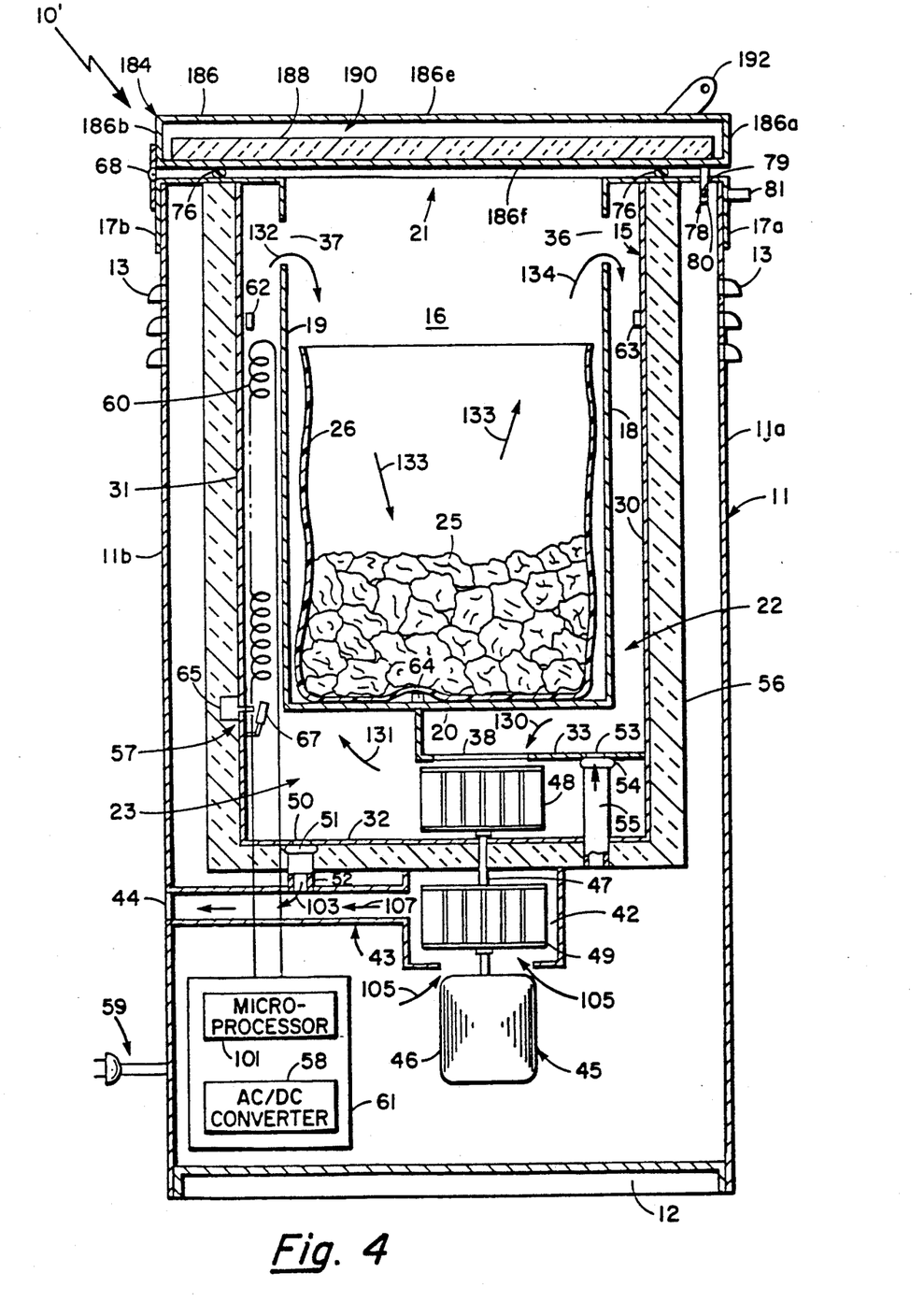
FIG. 4 is a side elevational view partly in section of a waste disposed system in accordance with an alternate embodiment of the present invention.

Referring now to FIG. 4, an alternate embodiment 10' of sterilizer 10 includes cabinet 11 and identical parts associated therewith as described above in conjunction with FIG. 1. However, in place of cover 66 (i.e. having drawer 82 disposed therein, FIG. 1), sterilizer 10' includes a simple cover arrangement 184. Cover 184 includes a frame 186, here, comprised of stainless steel and coupled to cabinet 11 by hinge 68. Outer frame 186 has a front wall 186a, rear wall 186b, side walls 186c and 186d (not shown), a top wall 186e, and a bottom wall 186f, as shown. A layer of insulation 188 is coupled to bottom wall 186f as shown to assist in retaining heat within sterilizer 10'. A vacant area, or air gap 190 is disposed between insulation 188 and cover frame 186. Air from outside of sterilizer 10' enters air gap 190 through openings in frame 184 (not shown) and flows therethrough by natural convection. Such air flow assists in keeping cover 184 at a safe temperature for contact during the sterilization process. Waste 25 is loaded into melting chamber 16 of sterilizer 10, by lifting cover 184 via a handle 192, as shown. The ultrasonic sensor 180 may be used in conjunction with cover 184 in a manner similar to that described above in conjunction with FIG. 1. Note that although the embodiment of FIG. 4 does not provide the operational flexibility provided by that of FIG. 1 (i.e. sterilizer 10' is operable in batch mode only), such sterilizer 10' may be desirable due to its manufacturing simplicity and thus, cost savings.

Once the medical waste 25 is deposited in melting chamber 16 of either the sterilizer embodiment of FIG. 1 or FIG. 4, the operator may commence the sterilization process. Here, disposed on the front wall 11a of cabinet 11 are three controls (not shown) adapted for actuation by the operator of sterilizer 10 (or 10'). These controls or, switches, include a power switch, a melting switch used to commence the melting process, and a cooling switch used to commence the cooling process. Each of the three switches has a corresponding indicator light which indicates whether power is on in the case of the power indicator light or whether the sterilizer 10 (or 10') is in the melting or cooling cycle in the case of the melting and cooling indicator lights, respectively. Also disposed on front wall 11a, is an additional indicator light which is lit when the sterilizer 10 is ready to receive waste material 25 and initiate the melting process, and thus such light may be referred to as a "ready" indicator light. The sterilization process is commenced by depressing the power switch. Here, this action causes heating element 60, blower motor 46, and interlocking mechanisms 78, 100, and 124 (i.e. for the sterilizer 10 of FIG. 1, or alternatively, interlocking mechanism 78 only for the sterilizer 10' of FIG. 4) to be activated. In other words, lid 92 and cover 66 (i.e. cover 184 for the sterilizer 10' of FIG. 4) will be locked in their closed positions during the sterilization process, as well as drawer 82 being locked in its forward position. With blower motor 46 activated, impeller 48 draws air in through aperture 38 from front air circulation chamber 22, as indicated by arrow 130. The air is expelled into rear air circulation chamber 23, as indicated by arrow 131. The air is further directed past activated heating element 60 and into melting chamber 16 through aperture 37, as shown by arrow 132. As indicated by arrows 133, the air entering melting chamber 16 interacts with the waste material 25 to heat such material 25. The heated air is then drawn out of melting chamber 16 through aperture 36 and into front air circulation chamber 22, as shown by arrow 134. The above described air circulation flow pattern is continuous while blower motor 46 is activated.

During an initial stage of the sterilization process, the heated air entering melting chamber 16 volatilizes the water content of the waste material 25 into steam. When the air inside chamber 16 reaches a temperature of approximately 212° F., valve 51 coupled to exhaust duct 52 is opened. The steam generated in melting chamber 16 is thus directed through aperture 50, valve 51, exhaust duct 52, and exhaust arrangement 43, as shown by arrow 103. With blower motor 46 activated, impeller 49 draws air into blower chamber 42, as indicated by arrows 105. The air thus directed comes from outside of cabinet 11 and enters cabinet 11 through inlets 13. Impeller 49 expels air through exhaust arrangement 43, as indicated by arrow 107. Here, microprocessor 101 controls the opening of valve 51 to yield a mixing ratio of air drawn through impeller 49 to air directed from rear air circulation chamber 23 of approximately 100:1.

Once the water content of the waste material 25 has been driven off, or vaporized, the temperature within chamber 16 rises to approximately 450° F. By exposing infectious waste material 25 to such a high temperature of approximately 450° F. for a duration of approximately fifteen minutes, the complete destruction of any infectious organisms is ensured. At 450° F., the bacteria is rendered harmless, the waste 25 is liquified, and its volume reduced. However, this temperature is significantly lower than the temperatures at which the plastic is molded and, as a result, the likelihood of toxic fumes evolving is minimized. Note that this duration corresponds to the time required to render the maximum volume of infectious waste harmless once the waste has reached a temperature of approximately 450° F. Furthermore, this high temperature melts the infectious waste 25, thus converting such waste 25 to a liquid state. The melting of waste material 25 provides a volume reduction of the waste material 25 of between approximately seventy and ninety percent. Thus, the plastic waste material 25 is rendered harmless, as well as unrecognizable as medical waste. Once the melting chamber 16 has been maintained at a temperature of approximately 450° F. for a sufficient length of time to ensure that all infectious waste has been sterilized, heating element 60 is de-activated, or shut off.

As mentioned above, when sterilizer 10 (FIG. 1) is operated in the continuous mode (i.e. by loading waste 25 into chamber 16 via drawer 82) ultraviolet lamp 114 may be used to assure that any waste 25 remaining in drawer 82 will be rendered harmless. In other words, it is possible, for example, that infectious fluids may leak out of plastic containers and onto the walls of drawer 82. While the waste 25 transferred from drawer 82 to chamber 16 will be exposed to bacteria killing temperatures (as verified by temperature sensing device 64), there may be concern that any waste remaining in drawer 82 may not be exposed to such temperatures. Thus, ultraviolet lamp 114 may be activated during and/or after the melting process, and before mechanisms 100 and 124 are unlocked, in order to sterilize any bacteria present in drawer 82. Alternatively, a lock mechanism (not shown) may be provided to lock the drawer 82 in the second position in which drawer 82 is disposed substantially above aperture 21 of melting chamber 16 during the sterilization process. In this way, the temperature to which drawer 82 is subjected during the sterilization process will be closer to the bacteria killing temperatures within the melting chamber 16.

In certain cases, the length of time during which infectious waste 25 is exposed to high temperatures in order to render such waste 25 harmless is shorter than the duration necessary to provide maximum volume reduction to the waste 25. In such cases, it may be desirable to expand the processing time beyond that required to sterilize the waste 25 in order to achieve maximum volume reduction. A convenient way of determining whether the volume of the waste has been maximally reduced is to utilize the ultrasonic sensor 180 referred to above. In other words, the heating element 60 can remain activated after the fifteen minute high temperature period has lapsed and for as long as a height reduction is sensed. More particularly, the sonic transducer 180 provides the control signal at the beginning of the melting cycle to indicate the initial height of the waste 25. The transducer 180 then, periodically provides such control signal until microprocessor 101 detects a constant height over a number of samples (i.e. indicating maximum volume reduction) at which time heating element 60 is de-activated. Alternatively, heating element 60 may be de-activated once microprocessor 101 detects a predetermined volume reduction of the plastic waste 25, for example a volume reduction of approximately 8:1. In other words, rather than exposing the waste 25 to high temperatures for a time period corresponding to the time required to sterilize the waste 25, such waste 25 is exposed to high temperatures for an additional period of time required to further reduce the volume of the waste 25.

Note that with the above-described melting process, the waste 25 will be exposed to a temperature in excess of 450° F. for at least approximately fifteen minutes, regardless of the volume of such waste 25. However, the total processing time will vary as a function of the water content of the waste 25 since the duration of the initial stage of the sterilization process (i.e. the stage during which the water content of the waste 25 is volitized) varies with such water content. In certain applications, it may be desirable to provide an indication for example, via an LCD display (not shown), of the duration of the sterilization process. This feature may be realized with the use of ultrasonic sensor 180 in cases where known waste material is to be sterilized. Consider, for example, the case where petri dishes with agar disposed therein are to be sterilized. By sensing the height of such waste, an approximation of the number of petri dishes and, thus, the total ratio of solid material to liquid (based on a predetermined amount of agar per petri dish) may be obtained. With such water content information, the amount of time necessary to vaporize the water content may be estimated based on the heat of vaporization of water and added to the fifteen minute bacteria sterilization time to estimate the total processing time.

After the melting cycle, microprocessor 101 controlled valve 54 coupled to inlet duct 55 is opened and heating element 60 is de-activated. Opening valve 54 causes air from outside cabinet 11 to be directed through inlets 13, inlet duct 55, and into front air circulation chamber 22. This relatively cool external air is drawn into impeller 48 through aperture 38, as shown by arrow 130. Thus, the air is directed through rear air circulation chamber 23, melting chamber 16, and front air circulation chamber 22; however, such air is not heated by heating element 60 since such element 60 is now shut off. In this way, the chamber 16, and more particularly, the molten medical waste 25 is cooled. The flow of cool air further causes the molten waste 25 to harden and solidify yielding an easily handled block of sterilized waste. Once the temperature inside chamber 16 decreases to a level which is safe for contact by operating personnel, the interlock mechanisms 78, 100, and 124 (i.e. in the case of sterilizer 10 of FIG. 1 and mechanism 78 only in the case of sterilizer 10' of FIG. 4) are released thereby enabling such personnel to raise cover 66 (or cover 184 for sterilizer 10' of FIG. 4) and remove the solidified block of sterilized waste material for further disposal in a landfill, if so desired.

Figure 5A:
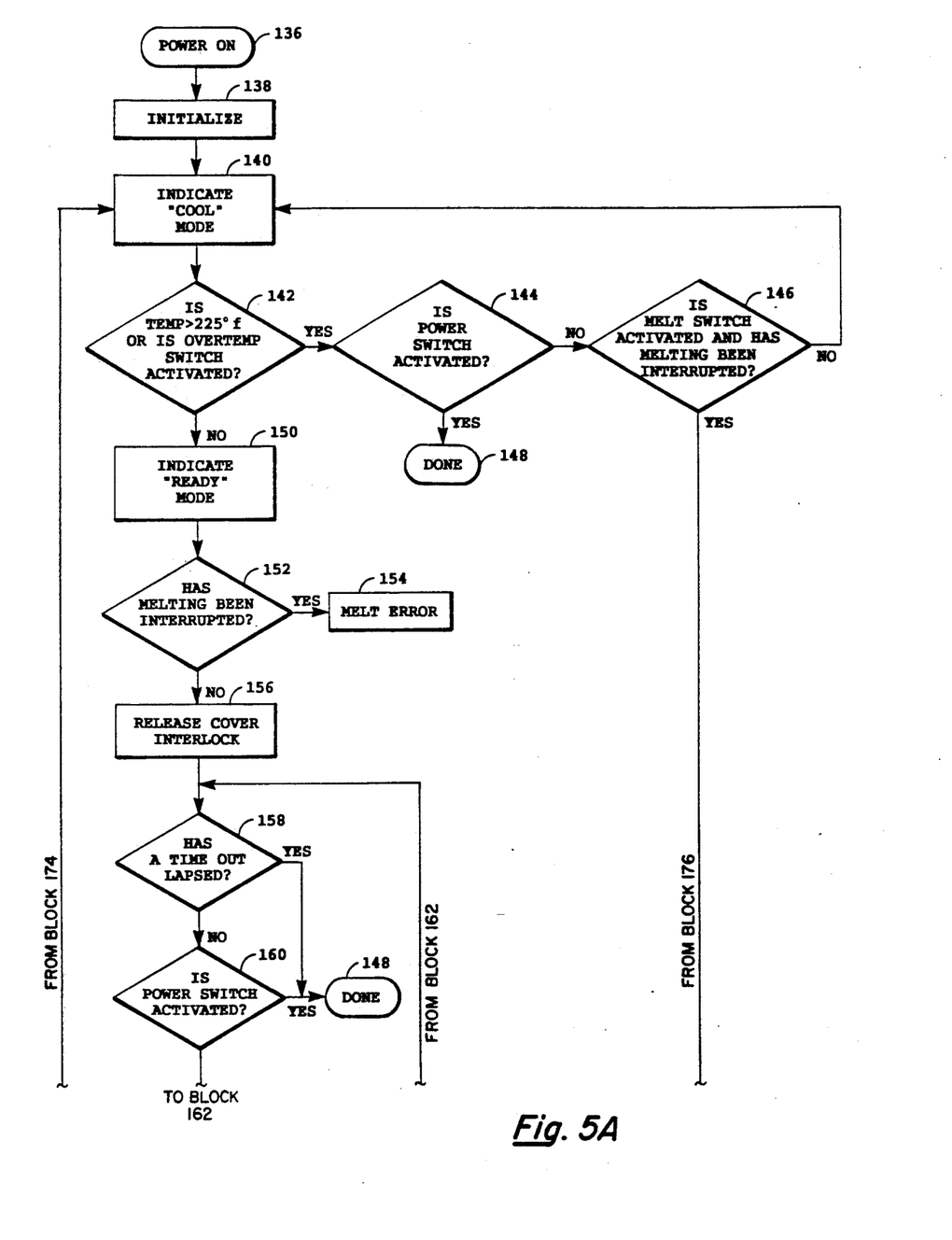
FIGS. 5A and B show a flow diagram of the operation of the waste disposal system of FIG. 1.
Figure 5B:
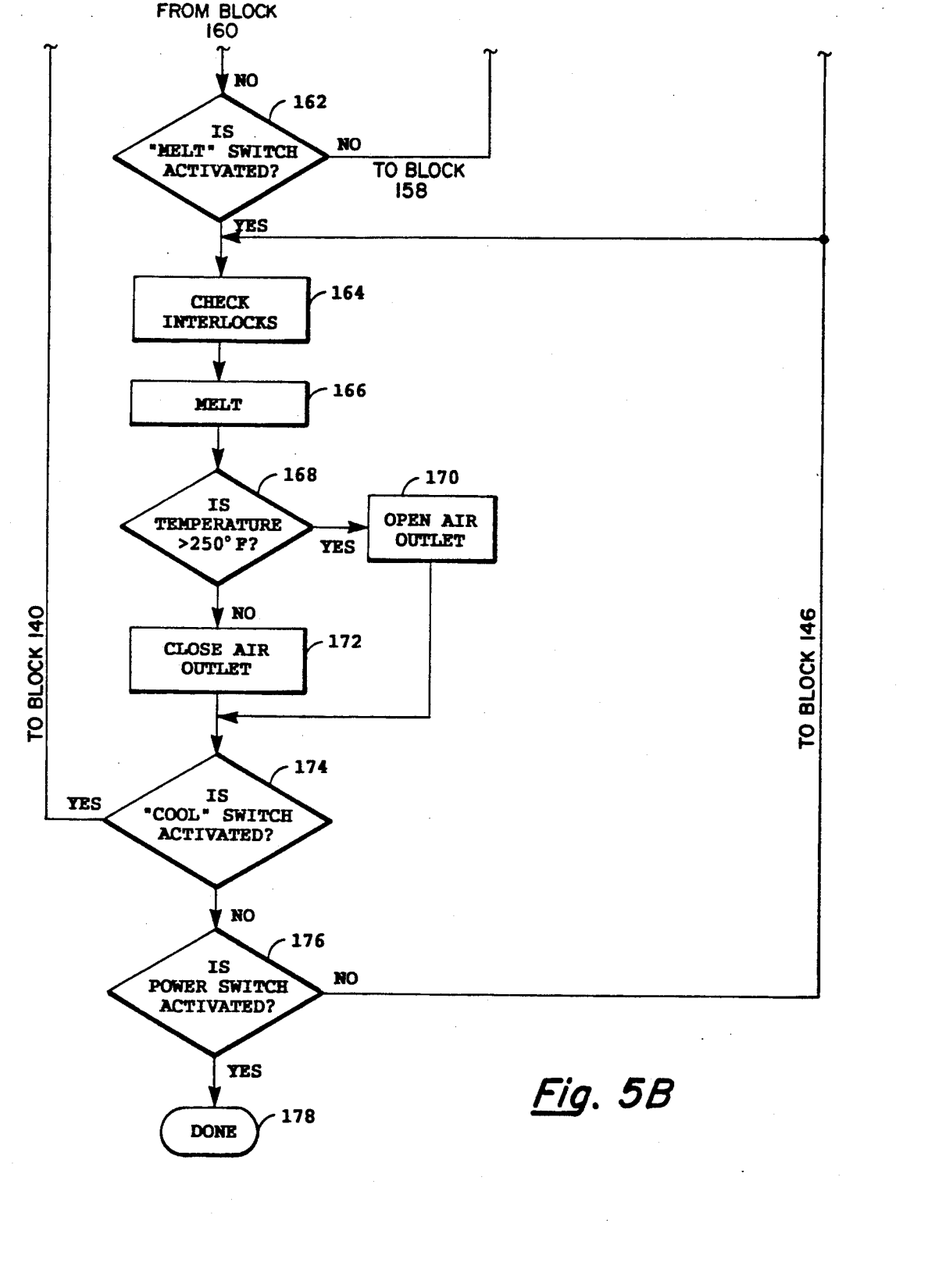

As mentioned, the control of the sterilization process, described generally above, is achieved with the use of microprocessor 101. Referring now to FIGS. 5A and 5B, the operation of sterilizer 10 (i.e. like that of sterilizer 10' of FIG. 4 except that cover 66 of sterilizer 10 corresponds to cover 184 of sterilizer 10' and lid 92 and drawer 82 are not present in sterilizer 10') will be described in detail in conjunction with a flow diagram of the operation of microprocessor 101. In step 136, the power switch is operator activated, thereby initiating step 138 in which microprocessor 101 is initialized. More particularly, in step 138, the internal registers of microprocessor 101 are cleared and the code with which the following steps are executed is loaded into random access memory (RAM) as is conventional. After initialization step 138, microprocessor step 140 is executed in which the indicator light corresponding to the cooling switch, or the cooling indicator light, is activated. With the cooling indicator light on, the operator of sterilizer 10 is notified that the apparatus 10 is disposed at a temperature sufficiently low to be safe for contact. Subsequently, in step 142, microprocessor 101 determines whether the temperature inside sterilizer 10 is greater than approximately 225° F. (by monitoring temperature sensing device 62) or whether the over temperature switch 63 has been activated. If the outcome of either of these determinations is true, or affirmative, microprocessor 101 executes step 144 in which it is determined whether the power switch has been activated. If the power switch has not been activated, microprocessor 101 next executes step 146; whereas, if the power switch has been activated, the process is done, as indicated by step 148 and power is shut off. With this arrangement, an operator of sterilizer 10 is permitted to shut off power, in step 144, during the cooling cycle.

As mentioned, if the power switch is not activated in step 144, step 146 is executed in which it is determined whether the melting switch is activated and whether the melting cycle has been interrupted. If both of these conditions are true, step 164 is next executed as will be described below. However, if the outcome of step 146 is false, or negative, as is the case during a cooling cycle which follows an uninterrupted melting cycle, microprocessor 101 will re-execute step 140 and will again indicate that the sterilizer 10 is in the cooling cycle via the cooling indicator light.

Consider now the case in which the outcome of step 142 is negative. In other words, the temperature, as monitored by temperature sensor 62, is less than approximately 225° F. and over temperature switch 63 has not been activated. In this case, microprocessor 101 executes step 150 in which the ready indicator light is activated, or lit thereby notifying the operator of sterilizer 10 that the apparatus is ready to process waste. Subsequently, step 152 is executed in which it is determined whether the melting cycle has been interrupted. If the melting cycle has been interrupted, microprocessor step 154 is executed.

Microprocessor step 154 includes several steps described hereinafter and simplified to "melt error" step 154 for improved clarity of FIG. 4. In step 154, the operator of sterilizer 10 is notified of a melting error. More particularly, both the melting indicator light and the cooling indicator light will flash on and off continuously to indicate an interrupt in the melting process. Such indication to the operator is particularly important so that infectious waste 25 is not mistaken for harmless waste having undergone a full melting cycle. In response to the flashing light indication corresponding to a melting error, the operator of sterilizer 10 may activate the melting switch which causes microprocessor 101 to execute step 166, as will be discussed below. The operator may alternatively depress the cooling switch in response to the flashing light indication of a melting error. Such action by the operator provides a reset mechanism which has the effect of returning microprocessor 101 to step 140.

In the case where it is determined, in step 152, that the melting cycle has not been interrupted, step 156 is executed subsequent to step 152. In step 156, the cover interlock 78 is released thereby permitting access to melting chamber 16. A predetermined length of time is then allowed to lapse, after which power is shut off to the sterilizer 10. More particularly, in step 158, it is determined whether the predetermined time duration has lapsed. In the case where such time lapse has occurred, microprocessor 101 executes step 148 in which power is shut off to sterilizer 10 and the process is done. However, until such time has lapsed, microprocessor 101 subsequently executes step 160, in which the power switch is monitored. If such power switch is activated during this time duration, again microprocessor 101 executes step 148 to shut off power to sterilizer 10. However, in the case where the power switch is not activated during the predetermined time, step 162 is executed in which the melting switch is monitored. If the melting switch is activated in step 162, microprocessor 101 executes step 164.

In step 164, the cover interlock 78 is monitored. More particularly, monitoring of cover interlock 78 in step 164 occurs either in response to the condition mentioned above, where such melting switch is activated prior to the predetermined time duration lapsing or, alternatively, in response to the melting switch being activated and the melting cycle having been interrupted, as described above in conjunction with step 146. If, however, the melting switch 162 is not activated in step 162, microprocessor 101 re-executes the sequence of steps described above, beginning with step 158, as shown.

Microprocessor step 164 includes several steps as described hereinafter. First, microprocessor 101 determines whether cover 66 and lid 92 are in their closed, or lowered positions and locked via interlock mechanisms 78 and 100, respectively (FIG. 1). In the case where the cover 66 and lid 92 are closed and locked, microprocessor 101 then determines whether there is air flow in sterilizer 10 by monitoring air flow switch 65 (FIG. 1), as described above. In the case where there is air flow in sterilizer 10, microprocessor 101 next executes the step 166. However, if there is no air flow or if interlock mechanisms 78 and 100 are not in their locked positions, heating element 60 is shut off and the melting indicator light is flashed on and off to indicate to the operator of sterilizer 10 that either the blower 45 is not operating or that cover 66 and/or lid 92 are not closed and locked. In response to such an indication, the operator may reset the sterilizer 10 by depressing the cooling switch. In this case, microprocessor 101 next re-executes step 150 and resumes operation from such step 150.

In step 166, the waste material 25 is melted. More particularly, step 166 includes a series of steps, the first of which is to determine whether the over temperature switch 63 has been activated. If such switch 63 has been activated, heating element 60 is shut off and an audio indicator is activated to alert the operator of sterilizer 10 of the over temperature condition. The audio indication continues until the over temperature switch 63 is de-activated (i.e. when the temperature goes below the set point thereof; here, approximately 525° F.) or until a predetermined time period has lapsed. Once the predetermined time period has lapsed, power is shut off to sterilizer 10.

Consider next the case where the over temperature switch 63 is de-activated. In this case, temperature sensor 64 is monitored to determine whether the temperature inside chamber 16 is greater than approximately 250° F. If such temperature is above approximately 250° F., an error flag is set so that any interruption of the melting process will be determined in step 152. Once the temperature, as monitored by sensor 64, is greater than approximately 450° F., a timer is incremented. Such timer is then monitored to determine whether a predetermined time, corresponding to the time required to render infectious waste 25 harmless, has lapsed. Once the temperature inside melting chamber 16 has been maintained above approximately 450° F. for a suitable length of time, for example fifteen minutes, the melt error flag is cleared.

Microprocessor step 168 follows the melting step 166, and in such step 168 it is determined whether the temperature inside sterilizer 10 as measured by temperature sensor 62 is greater than approximately 250° F. In the case where such temperature is above 250° F., exhaust valve 51 is opened and air is thus directed out of rear air circulation chamber 23, as described above in conjunction with FIG. 1. Once the temperature is less than approximately 250° F., step 172 is executed and valve 51 is closed. Microprocessor 101 then monitors the cooling switch in step 174 to determine whether it has been activated. In the case where such switch has been activated, microprocessor 101 returns to step 140 to re-execute the series of steps described above. If, however, the cooling switch has not been activated, microprocessor 101 monitors the power switch in step 176. If such power switch is activated, step 178 is executed and power is shut off to the sterilizer 10. If, however, such switch is not activated, microprocessor 101 returns to step 164 and re-executes the sequence of steps thereafter, as described above.

Having described preferred embodiments of the invention, it will now become apparent to one of skill in the art that other embodiments incorporating their concepts may be used. For example, it should be appreciated that significant variations to the flow diagram described above in conjunction with FIGS. 5A and 5B may be realized without departing from the concept of the invention. For example, in step 164, drawer interlock mechanism 124 may additionally be monitored ensure that the drawer 82 is locked in the forward position during the melting process. Moreover, it may be desirable to activate the ultraviolet lamp 114 during microprocessor step 166 for example. It is felt, therefore, that these embodiments should not be limited to disclosed embodiments but rather should be limited only by the spirit and scope of the appended claims.

What is claimed is:

1. Apparatus for sterilizing waste materials comprising:
    a cabinet having an inlet in communication with ambient air;
    a melting chamber disposed in said cabinet and having an aperture through which waste material is deposited;
    a cover disposed over said aperture;
    an air circulation system comprising:
    (a) a first air circulation chamber disposed on a first side of said melting chamber and communicating therewith;
    (b) a second air circulation chamber disposed on a second side of said melting chamber and communicating therewith;
    (c) a heating element disposed in said first air circulation chamber;
    (d) blower means for directing air into said first air circulation chamber, past said heating element, through said melting chamber, and into said second air circulation chamber;
    (e) inlet duct means coupled to said second air circulation chamber for directing ambient air from said inlet of said cabinet into said second air circulation chamber;
    (f) means coupled to said inlet duct means for opening and closing said inlet duct means; and
    (g) control means coupled to said heating element and said blower means for de-activating said heating element and activating said blower means when said inlet duct means is open.

2. The apparatus recited in claim 1 wherein said control means comprises a microprocessor.

3. Apparatus for sterilizing waste materials comprising:
    a cabinet;
    a melting chamber disposed within said cabinet and having an aperture through which waste material is deposited;
    an air circulation system comprising a heating element and blower means for directing air past said heating element and into said melting chamber:
    a drawer for loading waste material into said melting chamber through said aperture, said drawer having a bottom and a plurality of sides and being slidable between a first loading position and a second position in which said drawer is disposed substantially above said aperture, wherein said drawer is constructed for transferring said waste material into said melting chamber when said drawer is in the second position.

4. The apparatus recited in claim 3 further comprising a cover coupled to said cabinet and disposed over said aperture, wherein said drawer is coupled to said cover.

5. The apparatus recited in claim 3 further comprising interlock means for locking said drawer in the first loading position when said heating element is activated.

6. The apparatus recited in claim 3 further comprising a lid disposed over said drawer when said drawer is disposed in the first loading position.

7. The apparatus recited in claim 6 further comprising means for locking said lid in a closed position when said heating element is activated.

8. The apparatus recited in claim 6 wherein said lid is comprised of an ultraviolet transmissive material.

9. The apparatus recited in claim 3 wherein said bottom of said drawer is disposed in a substantially horizontal position when said drawer is in the first loading position and wherein said bottom is disposed in a tilted position when said drawer is in the second position.

10. The apparatus recited in claim 9 wherein said bottom of said drawer is hingedly coupled to said drawer.

11. The apparatus recited in claim 10 wherein said bottom of said drawer is hingedly coupled to a front side of said drawer so that when said drawer is slid to said second position, said bottom automatically tilts downward transferring said waste material from said drawer to said melting chamber.

12. Apparatus for sterilizing waste materials comprising:
   a cabinet;
   a melting chamber disposed within said cabinet, said melting chamber having an aperture through which waste material is deposited to a predetermined height;
   an air circulation system comprising a heating element and blower means, said blower means directing air past said heating element and into said melting chamber:
   a cover disposed over said aperture;
   sonic means disposed over said melting chamber and in alignment with said aperture for providing a control signal corresponding to said predetermined height of the waste material deposited in said chamber; and
   means responsive to said control signal for deactivating said heating element.

13. The apparatus recited in claim 12 further comprising:
   a drawer coupled to said cover for loading waste material into said melting chamber through said aperture, said drawer being moveable between a first loading position and a second position in which said drawer is disposed substantially above said aperture; and
   means responsive to said control signal for locking said drawer in the first loading position.

14. The apparatus recited in claim 12 further comprising:
   a drawer coupled to said cover for loading waste material into said melting chamber through said aperture, said drawer being moveable between a first loading position and a second position in which said drawer is disposed substantially over said aperture;
   a lid disposed over said drawer when said drawer is disposed in the first loading position; and
   means responsive to said control signal for locking said lid in a closed position.

15. The method recited in claim 12 wherein said sonic means is attached to said cover.

16. A method for sterilizing waste material in a cabinet comprising the steps of:
   providing a melting chamber in said cabinet, waste material being deposited in said melting chamber;
   providing a first air circulation chamber on a first side of said melting chamber and in communication with said melting chamber;
   providing a second air circulation chamber on a second side of said melting chamber and in communication with said melting chamber;
   providing a heating element in said first air circulation chamber;
   sensing the height of said waste material deposited in said melting chamber; and
   de-activating the heating element in response to said sensed height.

17. The method recited in claim 16 further comprising the steps of:
   depositing waste material into said melting chamber using a drawer, said drawer being moveable between a first loading position and a second position in which said drawer is disposed substantially above said aperture; and
   locking said drawer in the first loading position when said heating element is activated.

18. The method recited in claim 16 further comprising the steps of:
   depositing waste material into said melting chamber using a drawer, said drawer being moveable between a first loading position and a second position in which said drawer is disposed substantially above said aperture;
   providing a lid over said drawer; and
   locking said lid in a closed position when said heating element is activated.

* * * * *